(12) United States Patent
Fink et al.

(10) Patent No.: US 7,227,624 B2
(45) Date of Patent: Jun. 5, 2007

(54) METHOD AND APPARATUS FOR MONITORING THE CONDITION OF PLASMA EQUIPMENT

(75) Inventors: Steven T. Fink, Meza, AZ (US); Thomas Windhorn, Chandler, AZ (US)

(73) Assignee: Tokyo Electron Limited, Tokyo (JP)

( * ) Notice: Subject to any disclaimer, the term of this patent is extended or adjusted under 35 U.S.C. 154(b) by 442 days.

(21) Appl. No.: 10/484,723

(22) PCT Filed: Jul. 24, 2002

(86) PCT No.: PCT/US02/23477

§ 371 (c)(1), (2), (4) Date: May 11, 2004

(87) PCT Pub. No.: WO03/010517

PCT Pub. Date: Feb. 6, 2003

(65) Prior Publication Data

US 2004/0184028 A1 Sep. 23, 2004

Related U.S. Application Data

(60) Provisional application No. 60/307,174, filed on Jul. 24, 2001.

(51) Int. Cl.
*G01N 21/00* (2006.01)
(52) U.S. Cl. .......................................... 356/72; 118/712
(58) Field of Classification Search .................. 356/72; 427/8; 118/712
See application file for complete search history.

(56) References Cited

U.S. PATENT DOCUMENTS

| 5,536,359 | A | 7/1996 | Kawada et al. |
| 5,716,878 | A | 2/1998 | Turner et al. |
| 5,759,424 | A | 6/1998 | Imatake et al. |
| 5,948,983 | A | 9/1999 | Gogol, Jr. et al. |
| 5,985,032 | A | 11/1999 | Eriguch |
| 6,025,916 | A | 2/2000 | Quick et al. |
| 6,146,492 | A | 11/2000 | Cho et al. |
| 6,630,364 | B2 * | 10/2003 | Johnson .......................... 427/9 |
| 6,750,977 | B2 * | 6/2004 | Otsubo et al. .............. 356/632 |

* cited by examiner

*Primary Examiner*—Gregory J. Toatley, Jr.
*Assistant Examiner*—Kara Geisel
(74) *Attorney, Agent, or Firm*—Oblon, Spivak, McClelland, Maier & Neustadt, P.C.

(57) ABSTRACT

An apparatus (100) senses a degree of cleanliness of a plasma reactor having a chamber (102) containing a plasma (103) that emits light (104) during a process conducted in the chamber (102). The apparatus (100) also has a light sensing element (180), configured to sense an intensity of the light (104) emitted by the plasma (103) after the light (104) passes through a film (135) that accrues in the chamber (102) during the process, and to provide a light intensity indication signal, and an electronics assembly (170) configured to receive the light intensity indication signal and to provide an indication of the degree of cleanliness of the plasma reactor.

34 Claims, 5 Drawing Sheets

METHOD AND APPARATUS FOR MONITORING THE CONDITION OF PLASMA EQUIPMENT

CROSS-REFERENCE TO RELATED APPLICATIONS

This application is related to and claims priority to U.S. provisional application Ser. No. 60/307,174 filed Jul. 24, 2001, the entire contents of which are herein incorporated by reference.

BACKGROUND OF THE INVENTION

1. Field of the Invention

The present invention relates to sensors and sensing methods. More specifically, the invention relates to methods and apparatus for sensing and monitoring the accumulation of impurities or other film inside a process chamber.

2. Description of the Background

Manufacturers of semiconductor integrated circuits (ICs) are faced with intense competitive pressure to improve their products and as a result, pressure to improve the processes used to fabricate those products. This pressure in turn is driving the manufacturers of the equipment used by IC manufacturers to improve the performance of their equipment, and in particular to reduce the operating cost to users of their equipment.

One particular type of tool that is widely used, and is therefore particularly susceptible to these competitive pressures, is the plasma reactor. These reactors are used to remove material from a wafer by a process called plasma etching. The mechanisms of plasma etching are complex and it is essential to maintain and control the plasma parameters and chamber conditions. Maintenance and monitoring of plasma process chamber conditions is the focus of significant technological development in the industry.

One of the key factors affecting product quality and the productivity of plasma processes is the presence of defect forming particles and related contamination within a chamber within a plasma reactor. The accumulation of polymers and other byproducts of the etch process from process chamber components causes yields to drop and maintenance expenses to increase. The manufacturer of plasma reactors that can address these issues and consistently demonstrate superior process control and product quality is positioned to expand market share.

A first problem is how to monitor the accumulation of a film on plasma tools inside a plasma process chamber. During an etch process, complex chemical processes take place, including the chemical transformation of photoresist on the surface of a wafer being etched, the removal of surface material via mechanical and/or chemical processes. These processes create chemical species that deposit on the walls of the chamber and other surfaces within the chamber. This material accumulates over the course of etching many wafers until it reaches a thickness at which the film under internal stresses breaks up and flakes off. These flakes can then move around the chamber, landing on the production substrate, leading to an immediate defect. These flakes can also land on other vital surfaces such as system probes, where they can adversely affect system performance.

One way to solve the same problem is to dismantle the process chamber and visually inspect the pieces. However, this is extremely inefficient and costly because of the extended chamber downtime. Another way to solve the same problem is to use a spectrometer to look at emission of specific species. However, this can be more complicated and requires adjustment when utilizing different plasma conditions.

Therefore, there is a need in the art to simply and efficiently monitor the growth or accumulation of a film on plasma tools inside a plasma process chamber. Three patents disclose arrangements for monitoring the accumulation of films.

U.S. Pat. No. 6,146,492 (Cho et al), "Plasma process apparatus with in situ monitoring, monitoring method, and in situ residue cleaning method," appears to describe a plasma process apparatus and in situ monitoring method that is a complex approach having the disadvantage that a reactive gas must be injected into a chamber after a process has been completed, to allow the exiting gas to be analyzed to decipher the thickness of the wall film. A simpler approach allowing measuring of film accumulation is needed.

U.S. Pat. No. 6,025,916 (Quick et al.), "Wall deposition thickness sensor for plasma processing chamber," appears to describe a device for measuring polymer build-up on plasma chamber walls that involves the complex and indirect approach of monitoring interference patterns of light passing through a chamber window. A simpler and more direct approach is desirable.

U.S. Pat. No. 5,948,983 (Gogol, Jr. et al.), "Wall deposition monitoring system," appears to describe a wall deposit monitoring system for measuring variation in wall deposit thickness in an etch or deposition chamber. This complex method requires installation of a piezoelectric sensor on the chamber wall, and indirectly monitors contaminants by measuring vibration damping created by film accumulation. Again, a simpler and more direct approach to measuring film accumulation is desirable.

A second problem is how to optimize the scheduling of plasma chamber cleaning. Maintaining a clean chamber in a plasma etch tool is critical to producing integrated circuits (ICs) in a plasma etching process. Production efficiency depends in particular on the cleanliness of the process chamber. Conventional techniques for ensuring a clean chamber include operating the plasma chamber for a predetermined time and then dismantling the chamber for visual inspection. This technique does not account for changing plasma conditions and does not result in an accurate real-time representation of the chamber cleanliness. Inaccurate representations of the chamber cleanliness can result in product defects. Therefore, it is necessary to properly schedule maintenance to maximize production and maintain product quality. Therefore, there is a need in the art to optimize scheduling of plasma chamber cleaning.

A third problem is how to lower the cost of plasma etch processes. Maintenance and other non-productive time in a plasma etch system is extremely costly for manufacturers of semiconductor products. In addition, any defective product wastes valuable time and resources, increasing production costs. Therefore, there is a need in the art to lower the cost of plasma etch processes.

SUMMARY OF THE INVENTION

The present invention provides a method and apparatus for monitoring film build-up on the interior surfaces of a chamber such as a plasma process chamber.

A preferred embodiment of the invention provides an apparatus for sensing a degree of cleanliness of a plasma reactor having a chamber containing a plasma that emits light during a process conducted in the chamber. The apparatus comprises a light sensing element configured to sense an intensity of the light emitted by the plasma after the light passes through a film that accrues in the chamber during plasma generating processes, and to provide a light intensity indication signal; and an electronics assembly configured to receive the light intensity indication signal and to provide an indication of the degree of cleanliness of the plasma reactor based on the light intensity indication signal.

Likewise, the invention provides a preferred method of sensing a degree of cleanliness of a plasma reactor having a chamber containing a plasma that emits light during a process conducted in the chamber. The method involves sensing an intensity of the light emitted by the plasma after the light passes through a film that accrues in the chamber during the process, and providing a light intensity indication signal, and providing an indication of the degree of cleanliness of the plasma reactor based on the light intensity indication signal.

Alternate embodiments envision use of one or more light sources other than the plasma used in the semiconductor process itself, allowing testing of film accrual before and after the semiconductor process is conducted.

Alternate embodiments also envision use of plural light sensors located at respective locations in the chamber, to sense accrual of film at the respective locations.

A preferred method of monitoring a degree of accrual of a film in plasma chamber during a process conducted on semiconductor wafers in the plasma chamber, is also provided. The method involves loading a semiconductor wafer into the plasma chamber, starting the process on the loaded semiconductor wafer, and determining if the degree of accrual of the film has exceeded a threshold. If it is determined that the film has exceeded the threshold, then an alarm is triggered and the process is finished only for a current semiconductor wafer so as to allow a maintenance procedure to be performed on the chamber before the process is conducted on additional semiconductor wafers. If, however, it is determined that the film has not exceeded the threshold, then the process is completed and, if the process is to be conducted on additional semiconductor wafers, the loading and starting steps are carried out on the additional semiconductor wafers without first performing the maintenance procedure.

Thus, the present invention provides apparatus and methods to monitor the growth or accumulation of a film on plasma tools inside chambers such as a plasma process chamber, and to assess plasma process chamber cleanliness in real-time, to optimize scheduling of plasma chamber cleaning, and thus strategically reduce contamination to the product substrate, thus improving product quality and yield and thereby lowering the overall cost of processes such as plasma etch processes.

Other objects, features and advantages of the present invention will be apparent to those skilled in the art upon a reading of this specification including the accompanying drawings.

BRIEF DESCRIPTION OF THE DRAWINGS

The invention is better understood by reading the following Detailed Description of the Preferred Embodiments with reference to the accompanying drawing figures, in which like reference numerals refer to like elements throughout, and in which.

DETAILED DESCRIPTION OF THE PREFERRED EMBODIMENTS

Figure 1:
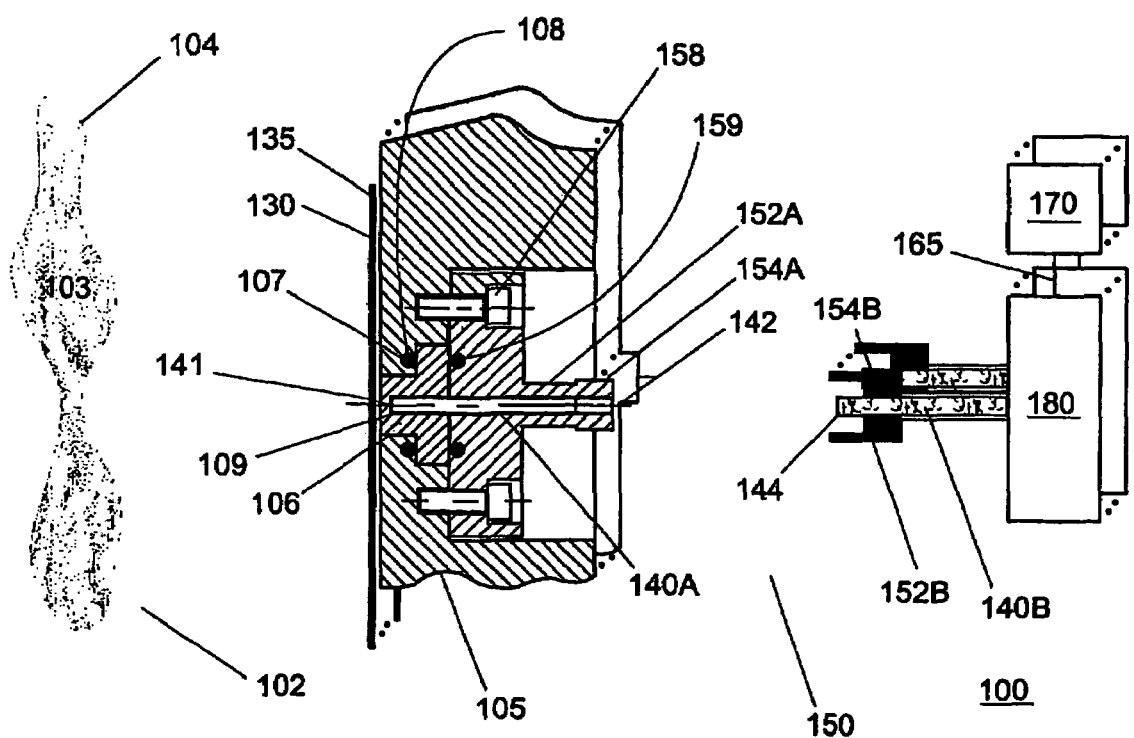
FIG. 1 shows a simplified schematic diagram of a plasma reactor illustrating various features of an exemplary embodiment of the present invention.

In describing preferred embodiments of the present invention illustrated in the drawings, specific terminology is employed for the sake of clarity. However, the invention is not intended to be limited to the specific terminology so selected, and it is to be understood that each specific element includes all technical equivalents that operate in a similar manner to accomplish a similar purpose.

FIG. 1 shows a simplified schematic diagram of a plasma reactor illustrating various features of an exemplary embodiment of the present invention. In FIG. 1, a portion of a plasma reactor is shown along with a chamber wall deposition monitoring apparatus. Monitoring apparatus 100 is used in conjunction with process chamber 102 that may be metal, and a process chamber wall 105 that includes at least one window 106 that is substantially transparent to light of wavelength emitted by plasma in process chamber 102. Process chamber wall 105 surrounds process chamber 102, and has an interior surface 130 on which film 135 grows during processes such as semiconductor substrate etching processes or deposition processes.

Only a portion of the process chamber and its walls are shown in FIG. 1 for purposes illustrating the invention's various features and not to photographically represent an actual process chamber. Thus, it is understood that FIG. 1 is schematic in nature and not literal, so that elements are not to scale.

As shown in FIG. 1, monitoring apparatus 100 comprises optical guides 140a and 140b, optical coupler 150, light detector 180, and electronics assembly 170. First optical guide 140a and a second optical guide 140b are collectively referred to herein as element 140.

Optical guide 140a has an optical entrance surface 141 and second optic end 142. Optical entrance surface 141 is located within window 106 in process chamber wall 105. As shown in FIG. 1, window 106 includes shoulder 107 and is mounted to a recess in chamber wall 105 using sealing O-ring 108.

Optical coupler 150 comprises first optical connector 152a and second optical connector 152b. First optical guide 140a is coupled to first optical connector 152a, and second optical guide 140b is coupled to second optical connector 152b. First optical connector 152a comprises first mating surface 154a that mates with mating surface 154b on second optical connector 152b, and the mating allows first optical guide 140a to be optically coupled to second optical guide 140b.

First optical connector 152a is coupled to chamber wall 105 using fastener 158 and cooling O-ring 159. For example, mating surfaces 154a and 154b can be threaded surfaces. In alternate embodiments, optical coupler 150 can include a light amplifier.

Second optical guide 140b comprises optic end 144 and is also optically coupled to light detector 180. For example, light detector 180 can be a commercially available silicon photodiode or similar type of diode having a wavelength detection range corresponding to the wavelength desired to be measured (in this example, 400 to 900 nanometers). When the intensity of the light is sensed using a photodiode, the light intensity indication signal is an electric current induced by light received by the photodiode.

Alternately, a unitary optical fiber (taking the place of separate elements) can be employed, and would not require the optical connectors between optic ends 142 and 144. However, splitting the optical guide 140 into two components, namely component 140a affixed within the chamber wall 105 and component 140b to optically connect the chamber optical site to a remotely located light detector 180, provides simpler design, assembly and maintenance.

Plasma etch process chamber 102 may be used, for example, for substrate etching processes disposed within any plasma processing device where excited species radiate energy. Such chambers include capacitively coupled plasma (CCP) and inductively coupled plasma (ICP) reactors, electron-cyclotron resonance (ECR) plasma sources, Helicon wave-heated plasma sources, etc. Process chamber wall 105 includes interior surface 130 on which film 135 accumulates.

Figure 2:
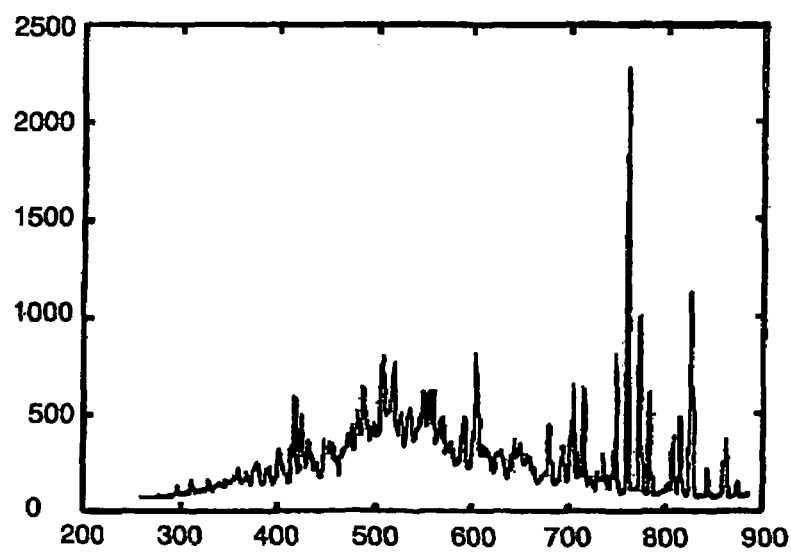
FIG. 2 illustrates a typical spectrum of emitted light, with wavelengths ranging from about 200 nm to about 900 nm (nanometers)

Plasma 103 is created in the etch process chamber 102 according to process conditions including gas species present, power applied, temperature, etc., in accordance with principles known to those skilled in the art. Plasma 103 emits light 104. The intensity and emission spectrum of the emitted light depends on the energy and chemical composition of the plasma. In one example, plasma is formed using a mixture of Ar, $C_4F_8$, $O_2$ and CO to achieve a plasma chemistry suitable for oxide (i.e. $SiO_2$) etch. This plasma produces a low amplitude, relatively broadband spectrum (shown in FIG. 2) on which peaks are superimposed corresponding to the gas species present.

Film 135 is a deposition of a mixture of polymer particles and other byproducts that is formed while plasma etching a substrate. The chemical composition of such films is not well understood by most equipment manufacturers, since the chemical composition of photoresist (a key player in the film materials formed on chamber walls) is typically not disclosed. Film 135 has a thickness that depends on process conditions and the amount of time that the etching process has been active.

In a preferred embodiment, optical guide 140a comprises an optical fiber having an optical entrance surface 141 and first optic end 142. Alternately, optical guide 140a can be a commercially available quartz rod or waveguide through which the emitted light is capable of being transmitted. Its dimensions may vary to correspond to the window's dimensions and the area of light detector 160. For example, when window thickness is approximately 10 mm, the optical fiber can have a diameter 1 to 3 mm and a length of 100 to 150 mm. Similarly, optical guide 140b can be a commercially available optical fiber (or fiber optic bundle) of diameter 1 to 3 mm and length of 500 to 1500 mm.

Transmission media 165 comprises a suitable medium for transmitting a signal that light detector 180 produces to indicate the quantity of light incident upon it, such as a shielded electrically-conductive wire.

Electronics assembly 170 includes a conventional arrangement of a CPU, memory and display collectively capable of processing and storing data and interfacing with a user. Desirably, electronics assembly 170 is capable of processing signals from light detector 180. For example, electronics assembly 170 is configured to receive consecutive light intensity indication signals over time, and to trigger an alarm when a light intensity indication signal indicates that the cleanliness of the plasma reactor has declined beneath a threshold value of cleanliness. Also, electronics assembly performs operations described below in further detail.

In the illustrated embodiment, window 106 is fabricated from quartz (transmittance for 1 mm thick GE 214 quartz spans approximately 180 to 4000 nm and transmittance for 1 cm thick GE 124 quartz spans approximately 200 to 3500 nm). Alternatively, window 106 is fabricated from alumina (transmittance for 2 mm thick crystalline or commercial grade aluminum oxide spans 200 to 6000 nm).

Window 106 is oriented with respect to plasma and its emitted light such that some of the emitted light passes through window 106, enters optical entrance surface 141, and is contained within first optical guide 140a. First optical guide 140a is positioned within window 106 such that optical entrance surface 141 is in close proximity to surface 130. In alternate embodiments, optical entrance surface 141 can be embedded within window 106.

Film 135 forms on exposed surfaces of process chamber wall 105, in particular on interior surface 130 and on window 106. Film 135 is the main mechanism by which light is attenuated before entering optical entrance surface 141. The amount of attenuation caused by window 106 is reduced by placing optical entrance surface 141 within recess 109 within window 106, thereby minimizing the effective thickness of the window 106 in the area immediately adjacent optical entrance surface 141.

In operation, upon formation of plasma, the plasma radiates emitted light, a portion of the emitted light passing through film 135 to be attenuated to a degree determined by the thickness of film 135. The attenuated emitted light passes through window 106 and is incident upon optical entrance surface 141. The attenuated incident light enters optical guide 140a and passes through optical guides 140a, 140b, until it impinges upon light detector 180. Light detector 180 transforms the portion of the attenuated emitted light it receives into an electric signal that travels via transmission media 165 to electronics assembly 170. Electronics assembly 170 stores and processes the signal, and presents a user with a suitable graphic, audible, and/or numeric display and/or alarm element(s) representing the state of cleanliness of the process chamber wall.

However, over time, plasma processes performed in chamber 102 cause film 135 to accumulate on interior surface 130 of process chamber wall 105 and window 106. As film 135 accumulates on interior surface 130 of process chamber wall 105 and window 106, a decreasing amount of emitted light is able to reach optical guide 140a. Over time, accumulated film 135 thus reduces the amount of emitted light that travels via optical guide 140b and reaches light detector 180. As a result of the film accumulation, light detector 180 sends progressively smaller signals via transmission media 165 to electronics assembly 170, which processes these signals and reports the increasing film accumulation to the user.

In alternative embodiments of the present invention, multiple optical sites with respective windows and optical entrance surfaces can be located in plural locations within the process chamber 102, along with corresponding optical guides and light detectors 180 that can send a plurality of signals to the electronics assembly 170. Electronics assembly 170 can process the plurality of signals and can report film accumulation to the user.

Figure 3:
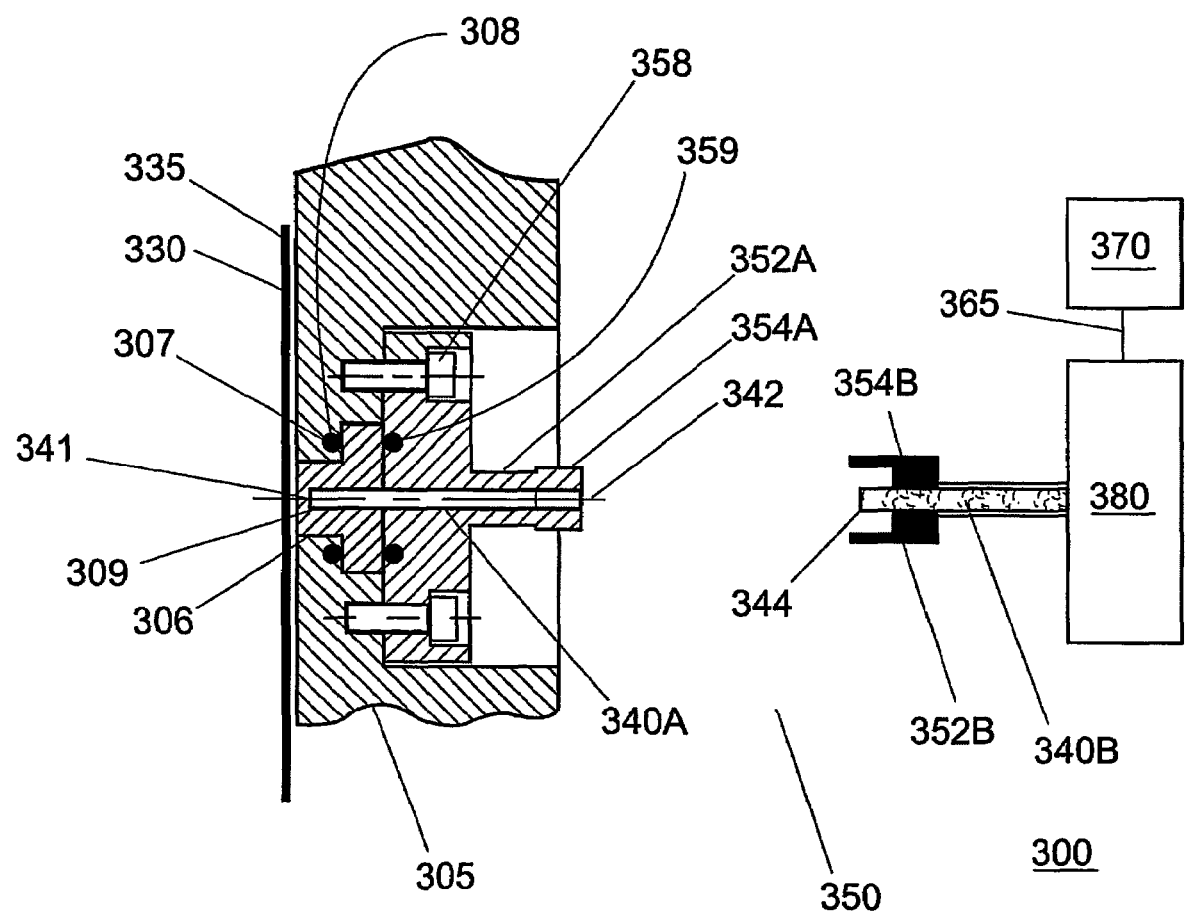
FIG. 3 shows a simplified schematic diagram of a plasma reactor illustrating various features of an alternate embodiment of the invention.

FIG. 3 shows a simplified schematic diagram of a plasma reactor illustrating various features of an alternate embodiment of the invention. In FIG. 3, a portion of the plasma reactor is shown along with an exemplary optical source 300. Optical source 300 is used in conjunction with process chamber 302 that may be metal, and process chamber wall 305 that includes at least one window 306 that is substantially transparent to light of wavelength emitted by optical source 300. Process chamber wall 305 surrounds process chamber 302, and has an interior surface 330 on which a film 335 grows during processes such as semiconductor substrate etching processes.

Only a portion of the process chamber and its walls are shown in FIG. 3 for purposes illustrating the invention's various features and not to photographically represent an actual process chamber. Thus, it is understood that FIG. 3 is schematic in nature and not literal so that elements are not to scale.

In an alternate embodiment, the monitoring apparatus (FIG. 1.) can include at least one optical source as shown in FIG. 3.

In the illustrated embodiment, optical source 300 comprises optical guides 340a and 340b, optical coupler 350, light source 380, and electronics assembly 370. First optical guide 340a and a second optical guide 340b that are collectively referred to herein as element 340.

First optical guide 340a comprises optical output surface 341, and second optic end 342. Optical output surface 341 is located within window 306 in process chamber wall 305. As shown in FIG. 3, window 306 includes shoulder 307 and is mounted to a recess in chamber wall 305 using sealing O-ring 308.

Optical coupler 350 comprises first optical connector 352a and second optical connector 352b. First optical guide 340a is coupled to first optical connector 352a, and second optical guide 340b is coupled to second optical connector 352b. First optical connector 352a comprises first mating surface 354a that mates with mating surface 354b on second optical connector 352b, and the mating allows first optical guide 340a to be optically coupled to second optical guide 340b.

First optical connector is coupled to chamber wall 305 using fastener 358 and cooling O-ring 359. For example, mating surfaces 354a and 354b can be snap-together surfaces. Alternately, optical coupler 350 can include a light amplifier.

Second optical guide 340b comprises optic end 344 and is also optically coupled to light source 380. For example, light source 380 is a semiconductor device.

Light source 380 is coupled to electronics assembly 370 using transmission medium 365. For example, light source 380 can be a commercially available light emitting device having a wavelength output range corresponding to the wavelength desired to be measured (in this example, 400 to 900 nanometers).

Film 335 is a deposition of a mixture of polymer particles and other byproducts that is formed while plasma etching a substrate. The chemical composition of such films is not well understood by most equipment manufacturers, since the chemical composition of photoresist (a key player in the film materials formed on chamber walls) is typically not disclosed. Film 335 has a thickness that depends on process conditions and the amount of time that the etching process has been active.

For example, optical guide 340a can be an optical fiber, or it can be a commercially available quartz rod or waveguide through which the emitted light is capable of being transmitted. Similarly, optical guide 340b can be a commercially available optical fiber (or fiber optic bundle) of diameter 1 to 3 mm and length of 500 to 1500 mm.

Transmission media 365 comprises a suitable medium for establishing an interface between electronics assembly 370 and light source 380. The interface being used to convey signals for determining, for example, the amount of light that light source 380 produces at a particular time.

Electronics assembly 370 includes a conventional arrangement of a CPU, memory and display collectively capable of processing and storing data and interfacing with a user as described earlier in reference to electronics assembly (170 FIG. 1) and further being capable of controlling light source 380.

Window 306 can be fabricated from quartz (transmittance for 1 mm thick GE 214 quartz spans approximately 180 to 4000 nm and transmittance for 1 cm thick GE 124 quartz spans approximately 200 to 3500 nm), or alumina (transmittance for 2 mm thick crystalline or commercial grade aluminum oxide spans 200 to 6000 nm).

For example, first optical guide 340a can be oriented with respect to first optical guide (140a FIG. 1) such that some of the emitted light at optical output surface 341 passes through the process chamber and enters optical entrance surface (141 FIG. 1) and is measured by a monitoring system as described above.

Window 306 is relatively transparent to light emitted by optical source 300. Film 335 forms on exposed surfaces of process chamber wall 305, in particular on interior surface 330 and on window 306. Film 335 is the main mechanism by which light from optical source 300 is attenuated before entering the chamber. The amount of attenuation caused by window 306 can be reduced by placing optical output surface 341 within recess 309, thereby minimizing the effective thickness of the window 306 in the area immediately adjacent optical output surface 341. Alternately, a unitary optical guide (taking the place of separate elements) can be employed. For example, splitting the optical guide into two components provides simpler design, assembly and maintenance.

In operation, upon command from electronics assembly 370, optical source 300 emits light, a portion of the emitted light passing through two layers of film 335 and being measured by a monitoring system as described above. The monitoring system uses the amount of attenuation to determine the thickness of the films.

Figure 4:
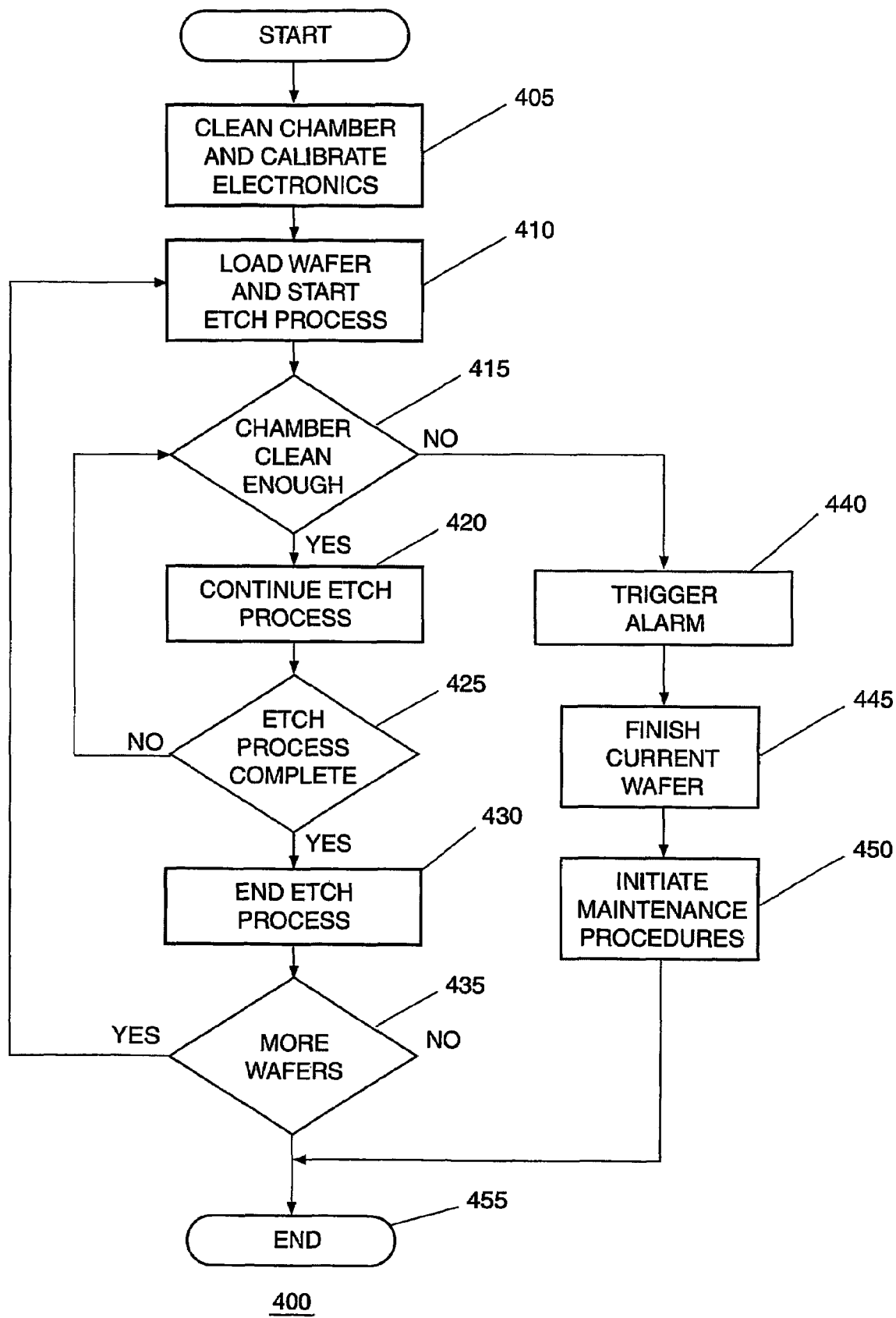
FIG. 4 is a flow chart showing steps in an exemplary plasma chamber film monitoring method.

FIG. 4 is a flow chart illustrating an exemplary plasma chamber film monitoring method according to the present invention.

After the start of the method, in step 405 the chamber is cleaned using manufacturer recommended methods along with cleaning steps to remove film 135 from interior surface 130 of process chamber wall 105. Typically, the chamber may be cleaned using an oxygen plasma or the chamber liner and components may be removed for a wet clean and replaced. At this time, electronics 170 may be calibrated to provide a reference to which changes in the signal created by light detector 180 can be compared. The calibration process of step 405 includes measuring the light detector response under process conditions to be used. If more than one process recipe is used in the reactor, then the response of light detector 180 for each process recipe is obtained to create a calibration chart. Moreover, the system may be calibrated using the external light source as described above. The calibration chart shows light intensities as a function of wall film thickness for every process scenario. Because the relationship is between light intensity and film thickness is known after experimentation, only a limited number of data points is needed to generate each correlation chart.

In step 410, a production wafer is loaded into process chamber 102 and placed on a wafer chuck (not shown), and the wafer etching process proceeds according to the process recipe selected for the wafer.

In decision step 415, electronics assembly 170 performs a comparison that determines whether the chamber is clean enough to continue normal process operation. As described above, light detector 180 converts the emitted light it receives into an electric signal, which is normally a value of electric current that is sensed by electronics 170. Electronics assembly 170 receives and stores the electric signal. Electronics assembly 170 then compares the value of the current to a threshold value 556 (see FIG. 5) determined by the calibration chart and the user. If threshold value 556 has been met or exceeded, then the system continues to step 220. If threshold value 556 has not been met or exceeded, then the system diverts to step 440, discussed below.

In step 420, the wafer continues to be etched within process chamber 102.

In decision step 425, a comparison is made to see if the wafer etching process has been completed. If the etching process has not been completed, then control is returned to step 415. If the etching process has been completed, then control passes to step 430. In step 430, the plasma etching process on one wafer terminates.

In step 435, if it is determined that there are more wafers to be processed, the control returns to step 410. If it is determined that there are no more wafers to be processed, then method ends, indicated by block 455.

In step 440, which is executed after decision block 415 determined that the chamber was not clean enough, electronics assembly 170 activates an indication or alarm alerting the user that film 135 has reached threshold response 557 (FIG. 5) and thus indicates process chamber wall 105 no longer meets the cleanliness standards defined by the calibration chart.

In step 445, the etching process of the current wafer is completed, and in step 450, a pre-determined maintenance protocol is initiated for the specific process that was completed in step 445. Finally, method 400 terminates, as indicated by block 455.

Figure 5:
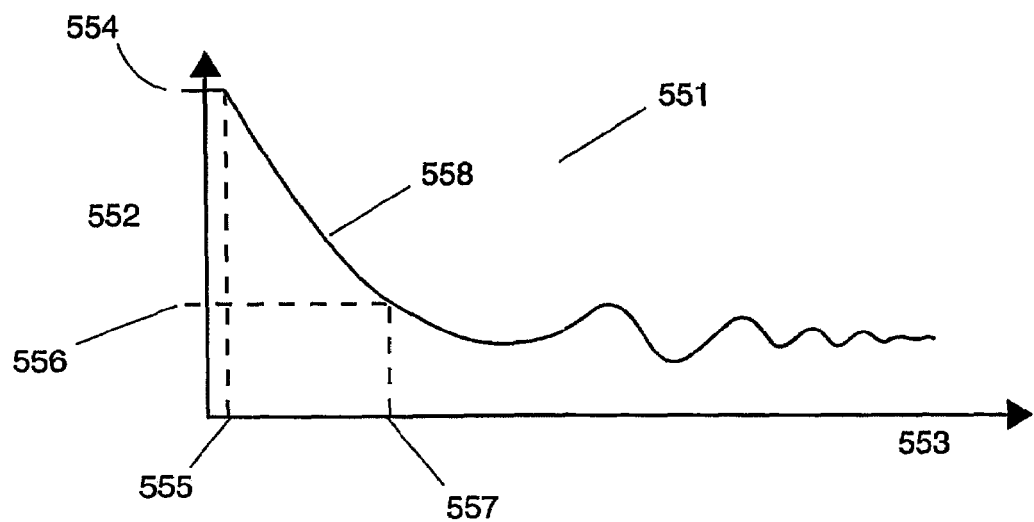
FIG. 5 illustrates a plot, as a function of etch-time, of a signal that indicates the current of the photodiode, which in turn indicates the accrual of film in plasma reactor.

FIG. 5 shows a plot of received signal versus etch-time. Received signal 552 is shown on the vertical axis, and etch-time 553 on the horizontal axis. A response curve 558 shows the relation of the received signal 552 and etch time 553, an initial value 554 of signal 552 at a time offset 555, a threshold value 556 of the signal 552 corresponding to a threshold response 557 as determined by response curve 558.

Signal versus etch-time plot 551 plots signal 552 versus etch-time 553 as response 558. Signal 552 is created by electronics assembly 170, and is based on a sensed parameter such as photodiode current. Offset 555 is the time in which response 558 settles to become a decipherable signal with an initial value 554. Response 558 then decays exponentially until reaching threshold value 556, which corresponds to threshold response 557.

Response 558 represents many data points that correspond to one or more measurements on individual wafers and measurements on one or more wafers. That is, it is expected that the reduction in signal 552 while etching any single wafer is slight. Below threshold value 556, noise in the form of uncontrolled changes in response 558 are due in part to flakes of film dislodging from a window, and, conversely, flakes of film dislodging from surfaces within the process chamber adhering to the window. Threshold response 557, which may be affected by system parameters such as plasma power, plasma gas composition and substrate materials, may be determined through experimentation by those skilled in the art.

Figure 6:
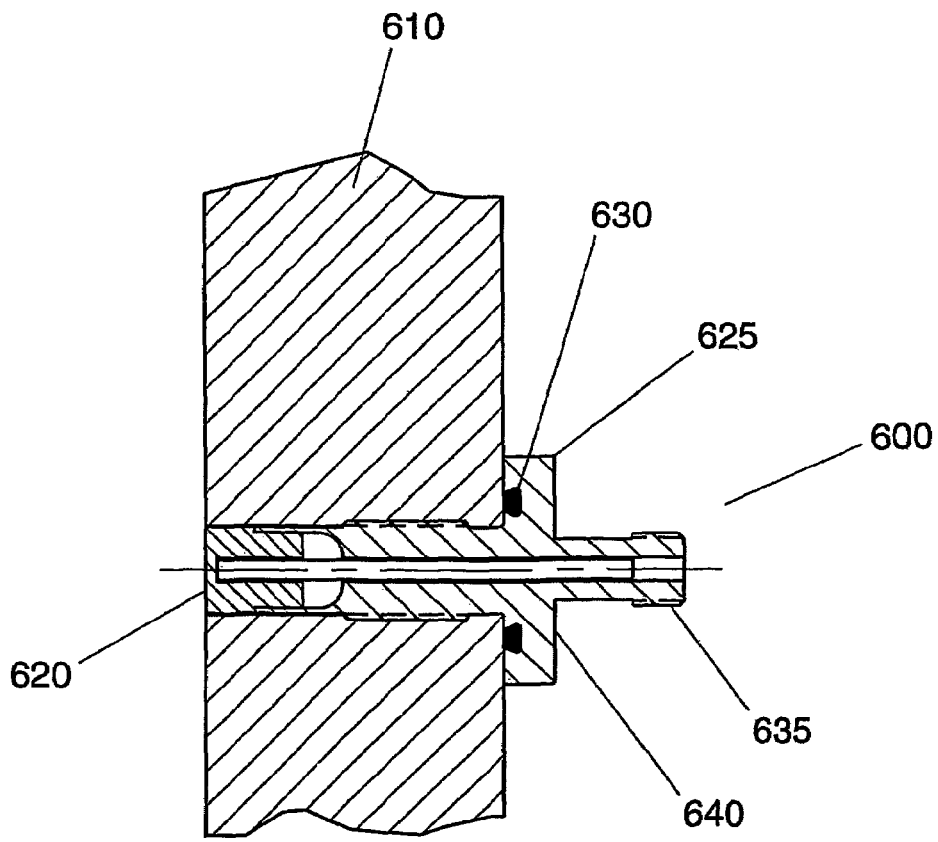
FIG. 6 illustrates a simplified schematic diagram of a Viewing Aperture Assembly (VAA) in accordance with another embodiment of the invention.

FIG. 6 illustrates a simplified schematic diagram of a Viewing Aperture Assembly (VAA) in accordance with another embodiment of the invention. VAA 600 is shown mounted in a process chamber wall 610. VAA 600 comprises tip 620 that is coupled to housing 625. For example, a ceramic tip can be brazed to a metal housing. Tip 620 can be fabricated from alumina or like ceramic material. Housing 625 is fabricated from stainless steel. The housing is threaded and is installed in an appropriate hole produced in the process chamber to receive the threaded feature. O-ring 630 seals the VAA as shown. A number of VAAs can be positioned in various locations around a chamber wall. Light passing through the VAA and the associated fiber to a photodiode is used to create a signal that represents the cleanliness of the reactor. The photodiode detects the intensity of the light and the apparatus compares the intensity values to a chart of known intensities for process conditions and film thickness. As film build-up increases on the window, the light intensity decreases.

Small cylindrical light passage 640 is located in the center of the housing and couples tip 620 to optical connector 635. Optical connector 635 is located at the end of the housing opposite the ceramic tip and is manufactured in a manner to produce features that can mate to optical cables attached to a photodiode assembly. The threaded joint is vacuum tight to a high vacuum level. VAA 600 provides an inexpensive replaceable monitoring assembly that functions as a sealed window in a process chamber and can be used in a monitoring system described herein. In alternate embodiments, VAA 600 can further comprise a light detector and/or a light source.

Figure 7:
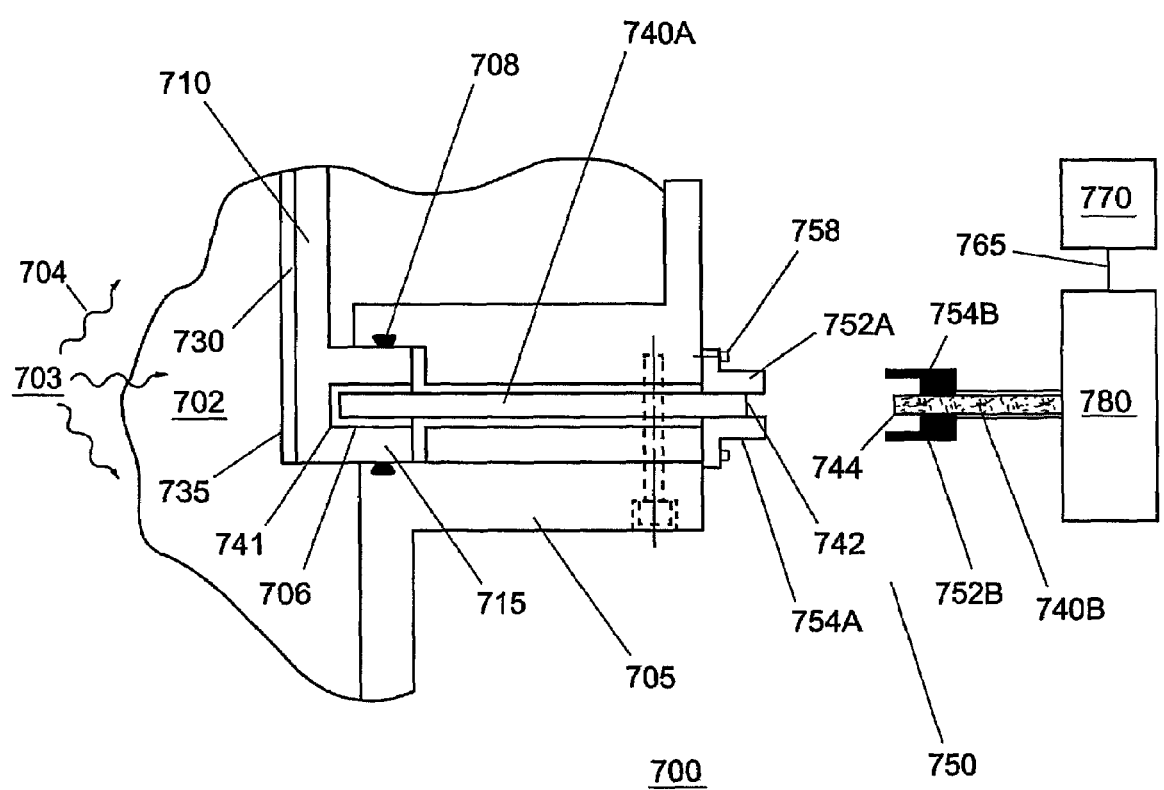
FIG. 7 illustrates a simplified schematic diagram of a plasma process tube in a plasma reactor illustrating various features of an alternate embodiment of the invention.

FIG. 7 illustrates a simplified schematic diagram of a plasma process tube in a plasma reactor illustrating various features of an alternate embodiment of the invention. In FIG. 7, a portion of a plasma reactor is shown along with a process tube based deposition monitoring apparatus. Monitoring apparatus 700 is used in conjunction with process tube that is mounted within process chamber 702. Process chamber can comprise metal, and process tube can comprise a material that is substantially transparent to light of wavelength emitted by plasma in process chamber 702. Process tube wall 710 surrounds process chamber 702, and has an interior surface 730 on which film 735 grows during processes such as semiconductor substrate etching processes or deposition processes.

Only a portion of the process chamber, the process tube, and their respective walls are shown in FIG. 7 for purposes illustrating the invention's various features and not to photographically represent an actual process chamber. Thus, it is understood that FIG. 7 is schematic in nature and not literal, so that elements are not to scale.

As shown in FIG. 7, monitoring apparatus 700 comprises optical guides 740*a* and 740*b*, optical coupler 750, light detector 780, and electronics assembly 770. First optical guide 740*a* and a second optical guide 740*b* are collectively referred to herein as element 740.

First optical guide 740*a* comprises optical output surface 741, and second optic end 742. Optical output surface 741 is located within recess 706 in the flange portion of process tube wall 710. As shown in FIG. 7, process tube wall 710 includes flange 715 and is mounted to a recess in chamber wall 705 using O-ring 708.

Optical coupler 750 comprises first optical connector 752*a* and second optical connector 752*b*. First optical guide 740*a* is coupled to first optical connector 752*a*, and second optical guide 740*b* is coupled to second optical connector 752*b*. First optical connector 752*a* comprises first mating surface 754*a* that mates with mating surface 754*b* on second optical connector 752*b*, and the mating allows first optical guide 740*a* to be optically coupled to second optical guide 740*b*.

First optical connector is coupled to chamber wall 705 using fastener 758. For example, mating surfaces 354*a* and 354*b* can be snap-together surfaces. Alternately, optical coupler 750 can include a light amplifier.

Second optical guide 740*b* comprises optic end 744 and is also optically coupled to light detector 780.

Film 735 is a deposition of a mixture of polymer particles and other byproducts that is formed while plasma etching a substrate. Film 735 has a thickness that depends on process conditions and the amount of time that the etching process has been active.

For example, optical guide 740*a* can be an optical fiber, or it can be a commercially available quartz rod or waveguide through which the emitted light is capable of being transmitted. Similarly, optical guide 740*b* can be a commercially available optical fiber (or fiber optic bundle) of diameter 1 to 3 mm and length of 500 to 1500 mm.

Transmission media 765 comprises a suitable medium for establishing an interface between electronics assembly 770 and light source 780. The interface being used to convey signals for determining, for example, the amount of light that light detector 780 detects at a particular time.

Electronics assembly 370 includes a conventional arrangement of a CPU, memory and display collectively capable of processing and storing data and interfacing with a user as described earlier in reference to electronics assembly (170 FIG. 1) and further being capable of controlling light detector 780.

Process tube wall 710 can be fabricated from quartz (transmittance for 1 mm thick GE 214 quartz spans approximately 180 to 4000 nm and transmittance for 1 cm thick GE 124 quartz spans approximately 200 to 3500 nm), or alumina (transmittance for 2 mm thick crystalline or commercial grade aluminum oxide spans 200 to 6000 nm).

Process tube wall 710 is relatively transparent to light emitted by the plasma. Film 735 forms on exposed surfaces of process tube wall 710, in particular on interior surface 730. Film 735 is the main mechanism by which light 704 emitted from plasma 703 is attenuated before entering recess 706. The amount of attenuation caused by process tube wall 710 can be reduced by placing optical output surface 741 within recess 706, thereby minimizing the effective thickness of the tube wall 710 in the area immediately adjacent optical output surface 741.

In alternative embodiments of the present invention, multiple optical sources can be used and can be located in plural locations around the process chamber, along with corresponding monitoring devices.

In other embodiments, one or more light sources can be provided inside the plasma chamber, directed at interior surface of process chamber wall to provide constant intensity light in lieu of plasma-emitted light. For example, electronics assembly assembles information from the one or more light sources and reports the degree of cleanliness of the chamber, possibly providing an alarm indication if cleanliness parameters (determined by experimentation and calibration) are violated.

Of course, the several monitoring systems and optical sources may be arranged and/or used in various combinations. Thus, it is not necessary to arrange an external light source 380 only with an optical output surface of type 341, and it is not necessary to arrange the monitoring device only with an optical entrance surface of type 141, since these are merely examples for purposes of explanation. It is emphasized that the arrangements of elements in FIG. 1 and FIG. 3 are illustrative and do not limit the invention.

As a further feature, a light source, which may be an external light source, can be employed when the plasma is turned off to couple light onto interior surfaces of the process chamber to illuminate the interior volume in order to check/calibrate wall monitoring sites from wafer-to-wafer, between cleaning cycles, etc.

Modifications and variations of the above-described embodiments of the present invention are possible, as appreciated by those skilled in the art in light of the above teachings. For example, varying the location and number of optical entrance surfaces, optical paths, and light detecting elements lies within the contemplation of the present invention. Also, the particular light source used to generate light that is passed through the film for attenuation, the particular way in which attenuated light is transmitted to a light sensor, the particular manner in which light intensity is detected and communicated, and the particular way in which the detected light level is communicated, stored, processed and reported to a user, may be varied while remaining within the scope of the invention. It is therefore to be understood that, within the scope of the appended claims and their equivalents, the invention may be practiced otherwise than as specifically described.

The invention claimed is:

1. An apparatus for sensing a degree of cleanliness of a plasma reactor having a chamber containing a plasma that emits light during a process conducted in the chamber, the apparatus comprising:
   a light sensing element, configured to sense an intensity of the light emitted by the plasma after the light passes through a film that accrues in the chamber during the process, and to provide a light intensity indication signal; and
   an electronics assembly configured to receive the light intensity indication signal, to compare the light intensity indication signal with a predetermined threshold and to provide an indication of the degree of cleanliness of the plasma reactor based on the result of the comparing.

2. The apparatus of claim 1, wherein:
   the light sensing element is a photodiode; and
   the light intensity indication signal is an electric current induced by light received by the photodiode.

3. The apparatus of claim 1, further comprising:
   an optical path extending from an interior surface of the chamber to the light sensing element, the optical path including an optical entrance surface located behind the accrued film so as to receive emitted light that has been diminished in intensity by being passed through the film.

4. The apparatus of claim 1, wherein the electronics assembly is configured to receive consecutive light intensity indication signals over time, and to trigger an alarm when a light intensity indication signal indicates that the cleanliness of the plasma reactor has declined beneath a threshold value of cleanliness.

5. The apparatus of claim 1, wherein:
the process is a semiconductor etching process during which the film accrues on walls of the chamber.

6. The apparatus of claim 1, further comprising:
a second light sensing element, configured to sense a second intensity of the light emitted by the plasma after the light passes through a film that accrues at a second location in the chamber, and to provide a second light intensity indication signal indicative of the degree of film accrual at the second location.

7. The apparatus of claim 1, wherein:
the light sensing element includes a light passage tube embedded in a window of the plasma reactor chamber.

8. An apparatus for sensing a degree of cleanliness of a chamber in which a process is conducted, the apparatus comprising:
a light emitting element configured to emit light;
a light sensing element, configured to sense an intensity of the emitted light after the light passes through a film that accrues in the chamber during the process, and to provide a light intensity indication signal; and
an electronics assembly configured to receive the light intensity indication signal, to compare the light intensity indication signal with a predetermined threshold and to provide an indication of the degree of cleanliness of the chamber based on the result of the comparing.

9. The apparatus of claim 8, wherein the light emitting element is disposed within the chamber.

10. The apparatus of claim 8, wherein the light emitting element is disposed outside the chamber and emits light through a wall of the chamber so that a portion of the emitted light enters the light sensing element.

11. The apparatus of claim 8, further comprising:
a second light sensing element configured to sense a second light intensity of light that passes through film that accrues at a second location in the chamber, and to provide a second light intensity indication signal indicative of the degree of film accrual at the second location.

12. The apparatus of claim 8, wherein:
the light sensing element includes a light passage tube embedded in a window of the plasma reactor chamber.

13. A method of sensing a degree of cleanliness of a plasma reactor having a chamber containing a plasma that emits light during a process conducted in the chamber, the method comprising:
sensing an intensity of the light emitted by the plasma after the light passes through a film that accrues in the chamber during the process, and providing a light intensity indication signal;
comparing the light intensity indication signal with a predetermined threshold; and
providing an indication of the degree of cleanliness of the plasma reactor based on the result of the comparing.

14. The method of claim 13, wherein:
the sensing step includes sensing the intensity of the light using a photodiode; and
the light intensity indication signal is an electric current induced by light received by the photodiode.

15. The method of claim 13, further comprising:
carrying some of the light emitted by the plasma along an optical path extending from an interior surface of the chamber to the light sensing element, the optical path including an optical entrance surface located behind the accrued film so as to receive emitted light that has been diminished in intensity by being passed through the film.

16. The method of claim 13, further comprising:
receiving consecutive light intensity indication signals over time, and
triggering an alarm when a light intensity indication signal indicates that the cleanliness of the plasma reactor has declined beneath a threshold value of cleanliness.

17. The method of claim 13, wherein:
the process is a semiconductor etching process during which the film accrues on walls of the chamber.

18. The method of claim 13, wherein:
the sensing uses a light passage tube embedded in a window of the plasma reactor chamber to sense the intensity of the light emitted by the plasma after the light passes through the film that accrues in the chamber during the process.

19. A method of sensing a degree of cleanliness of a chamber during a process conducted in the chamber, the method comprising:
emitting light into the chamber;
sensing an intensity of the emitted light after the emitted light passes through a film that accrues in the chamber during the process, and providing a light intensity indication signal;
comparing the light intensity indication signal with a predetermined threshold; and
providing an indication of the degree of cleanliness of the chamber based on the result of the comparing.

20. The method of claim 19, wherein the emitting step includes:
emitting the light into the chamber with a light emitting element that is disposed within the chamber.

21. The method of claim 19, wherein the emitting step includes:
with a light emitting element that is disposed outside the chamber, emitting the light through a wall of the chamber so that a portion of the emitted light is sensed in the light intensity sensing step.

22. The method of claim 19, further comprising:
sensing a second intensity of light that passes through film that accrues at a second location in the chamber, and providing a second light intensity indication signal indicative of the degree of film accrual at the second location.

23. The method of claim 19, wherein:
the sensing uses a light passage tube embedded in a window of the plasma reactor chamber to sense the intensity of the light emitted by the plasma after the light passes through the film that accrues in the chamber during the process.

24. A method of monitoring a degree of accrual of a film in a chamber in which a process is conducted on semiconductor wafers using a light intensity indication signal, the method comprising:
loading a semiconductor wafer into the plasma chamber;
starting the process on the loaded semiconductor wafer;
determining if the light intensity indication signal has exceeded a threshold;

if it is determined that the light intensity indication signal has exceeded the threshold, then triggering an alarm and finishing the process only for a current semiconductor wafer so as to allow a maintenance procedure to be performed on the chamber before the process is conducted on additional semiconductor wafers; and if it is determined that the light intensity indication signal has not exceeded the threshold, then completing the process and, if the process is to be conducted on additional semiconductor wafers, carrying out the loading and starting steps on the additional semiconductor wafers without first performing the maintenance procedure.

25. The method of claim 24, wherein the film accrual degree determining step includes:

sensing an intensity of emitted light after the emitted light passes through the film that has accrued in the chamber during the process, and providing a light intensity indication signal that is indicative of the degree of accrual of the film.

26. The method of claim 25, wherein:

plasma in the chamber emits light during the process conducted on the semiconductor wafers; and the emitted light intensity sensing step includes sensing the intensity of the light emitted by the plasma after the emitted light passes through the film that has accrued in the chamber.

27. The method of claim 25, wherein:

a light emitting element disposed within the chamber emits light; and the emitted light intensity sensing step includes sensing the intensity of the light emitted by the light emitting element after the emitted light passes through the film that has accrued in the chamber.

28. The method of claim 25, wherein:

a light emitting element disposed outside the chamber emits light into the chamber; and the emitted light intensity sensing step includes sensing the intensity of the light emitted by the light emitting element after the emitted light passes through the film that has accrued in the chamber.

29. The method of claim 25, wherein:

the emitted light intensity sensing step includes sensing the intensity of the light emitted at plural locations in the chamber after the emitted light passes through film that has accrued at the plural locations in the chamber.

30. A viewing aperture assembly (VAA) for sensing a degree of cleanliness of a plasma reactor having a chamber containing a source that emits light during a process conducted in the chamber, the VAA comprising:

a threaded housing including 0-ring for coupling to a threaded opening in a chamber wall a transparent tip coupled to the threaded housing;

an optical connector coupled to the threaded housing; and a light passage tube embedded in the transparent tip and coupled to the optical connector, the VAA being configured to sense an intensity of the light emitted by the source after the light passes through a film that accrues in the chamber during the process, and to provide a light intensity indication signal.

31. The apparatus of claim 30, further comprising:

a light sensing element configured to sense a light intensity of light that passes through film that accrues at a location in the chamber, and to provide a light intensity indication signal indicative of the degree of film accrual at the second location.

32. The apparatus of claim 30, further comprising:

a light emitting element configured to emit light into the chamber.

33. An apparatus for sensing a degree of cleanliness of a plasma reactor having a process tube containing a plasma that emits light during a process conducted in the process tube, the apparatus comprising:

a light sensing element, configured to sense an intensity of the light emitted by the plasma after the light passes through a film that accrues in the process tube during the process, and to provide a light intensity indication signal; and an electronics assembly configured to receive the light intensity indication signal, to compare the light intensity signal with a predetermined threshold and to provide an indication of the degree of cleanliness of the plasma reactor based on the result of the comparing.

34. The method of claim 24, wherein:

the determining uses a light passage tube embedded in a window of the plasma reactor chamber to obtain the light intensity indication signal.

* * * * *